(12) United States Patent
Ouyang et al.

(10) Patent No.: US 12,422,419 B2
(45) Date of Patent: Sep. 23, 2025

(54) SELF-CALIBRATING APPARATUS FOR SENSOR

(71) Applicant: SHENZHEN CAMBRI ENVIRONMENTAL TECHNOLOGY CO. LTD., Guangdong (CN)

(72) Inventors: Bin Ouyang, Guangdong (CN); Ziqiang Guo, Guangdong (CN); Wenyu Li, Guangdong (CN); Yuzheng Wang, Guangdong (CN)

(73) Assignee: SHENZHEN CAMBRI ENVIRONMENTAL TECHNOLOGY CO. LTD., Shenzhen (CN)

( * ) Notice: Subject to any disclaimer, the term of this patent is extended or adjusted under 35 U.S.C. 154(b) by 330 days.

(21) Appl. No.: 18/339,524

(22) Filed: Jun. 22, 2023

(65) Prior Publication Data
US 2023/0417718 A1    Dec. 28, 2023

(30) Foreign Application Priority Data
Jun. 28, 2022 (CN) .......................... 202210741885.5

(51) Int. Cl.
G01N 33/00 (2006.01)

(52) U.S. Cl.
CPC ..... *G01N 33/0006* (2013.01); *G01N 33/0027* (2013.01); *G01N 33/0059* (2013.01); *G01N 33/006* (2013.01)

(58) Field of Classification Search
CPC .......... G01N 33/0006; G01N 33/0027; G01N 33/0059; G01N 33/006
See application file for complete search history.

(56) References Cited

U.S. PATENT DOCUMENTS

| 3,864,628 A | 2/1975 | Klass et al. |
| 4,063,446 A * | 12/1977 | Fuhrmann .............. G01N 27/12 73/31.06 |
| 5,413,097 A | 5/1995 | Birenheide et al. |

(Continued)

FOREIGN PATENT DOCUMENTS

| CN | 102866232 | 1/2013 |
| CN | 102928485 | 2/2013 |

(Continued)

OTHER PUBLICATIONS

2nd Office Action from related Chinese Application No. 202210741885. 5, mailed Sep. 25, 2024. English translation attached.

(Continued)

*Primary Examiner* — Nathaniel J Kolb
(74) *Attorney, Agent, or Firm* — Grossman, Tucker, Perreault & Pfleger, PLLC

(57) ABSTRACT

A self-calibrating apparatus for a sensor. The apparatus includes a gas sensor assembly, a membrane assembly and a driving assembly. The membrane assembly is disposed opposite to the gas sensor assembly. The driving assembly is disposed between the gas sensor assembly and the membrane assembly and is configured to selectively connect the membrane assembly with the gas sensor assembly or separate the membrane assembly from the gas sensor assembly.

10 Claims, 3 Drawing Sheets

(56) References Cited

U.S. PATENT DOCUMENTS

| | | | | |
|---|---|---|---|---|
| 2022/0136994 A1* | 5/2022 | Ouyang | ............. | G01N 33/0039 |
| | | | | 702/24 |
| 2023/0213491 A1* | 7/2023 | Romanytsia | ....... | G01N 33/0032 |
| | | | | 73/1.06 |

FOREIGN PATENT DOCUMENTS

| | | |
|---|---|---|
| CN | 208519515 | 2/2019 |
| CN | 111157676 | 5/2020 |
| CN | 111487304 | 8/2020 |
| CN | 112352153 | 2/2021 |
| CN | 213666356 | 7/2021 |
| CN | 113866241 | 12/2021 |
| CN | 215070074 | 12/2021 |
| EP | 3978910 | 4/2022 |
| EP | 3978911 | 4/2022 |
| JP | 2006-29994 | 2/2006 |
| WO | 2022/002979 | 1/2022 |

OTHER PUBLICATIONS

Extended European Search Report from related EPO Application No. 23179529.5, mailed Nov. 10, 2023.
Office Action from related EPO Application No. 23179529.5, mailed Aug. 6, 2024.
Office Action from related Chinese Application No. 202210741885.5, mailed Jun. 13, 2024. English translation attached.

* cited by examiner

SELF-CALIBRATING APPARATUS FOR SENSOR

CROSS-REFERENCE TO RELATED APPLICATION

The present application claims the priority of the Chinese patent application No. 202210741885.5 which is titled as "SELF-CALIBRATING APPARATUS FOR SENSOR" and filed by SHENZHEN CAMBRI ENVIRONMENTAL TECHNOLOGY CO. LTD. on Jun. 28, 2022, which is hereby incorporated by reference in its entirety.

FIELD

The present disclosure relates to the technical field of self-calibrating apparatuses for sensors, and more particularly, to a self-calibrating apparatus for a sensor.

BACKGROUND

In related technologies, a small gas sensor is often used to detect different target gases in the environment. However, output reading of small gas sensors is easy to be affected by its own zero drift and the change in ambient temperature and relative humidity, resulting in a less accurate detection of the target gas.

SUMMARY

The present disclosure aims to solve at least one of the technical problems existing in prior arts. Therefore, one purpose of the present disclosure is to propose a self-calibrating apparatus for a gas sensor, which has the ability to independently calibrate the sensor's responses to the change in ambient temperature and humidity, and the ability to calibrate its zero line, so as to improve detection accuracy.

A self-calibrating apparatus for a sensor is provided according to an embodiment of the present disclosure. The self-calibrating apparatus for the sensor includes a gas sensor assembly, a membrane assembly, and a driving assembly. The membrane assembly is disposed opposite to the gas sensor assembly. The driving assembly is disposed between the gas sensor assembly and the membrane assembly and is configured to selectively connect the membrane assembly with the gas sensor assembly or separate the membrane assembly from the gas sensor assembly.

With the self-calibrating apparatus for the sensor according to the embodiment of the present disclosure, the driving assembly can move the membrane assembly and cause it to be in gas-tight contact with or be separated from the gas sensor assembly, thus the membranes in the membrane assembly can selectively cover or not cover the sensing surface of the gas sensors, so as to obtain different detection results based on the different air components that can or cannot permeate through the membranes. These different detection results can then be combined to allow for accurate calibration of the responses of the gas sensors to, e.g. the constantly changing ambient temperature and humidity, and the baseline position of the gas sensors, thus reducing the uncertainty of the measurements by the gas sensor assembly.

For instance, when the membrane is chosen to be a selective water permeable membrane (such as the Nafion™ membrane), one that allows the water vapour to permeate through highly effectively but not most of the target gases of atmospheric or health exposure interests such as carbon monoxide, nitric oxide, nitrogen dioxide or ozone, the sensor covered will be responsive to the change in relative humidity (since water vapour in the ambient air can still get in and out of the sensor almost freely) but not the target gases. Sensor users can therefore isolate the "change in relative humidity" effect and set up correct algorithm(s) to correct for it in later measurements of target gases when the sensor is not covered by the membrane and is responsive to both relative humidity and gas.

In some embodiments, the driving assembly includes a driving member, a first transmission member and a second transmission member. The driving member is disposed on one of the gas sensor assembly and the membrane assembly. The first transmission member is disposed on the driving member. The second transmission member is in transmission fit with the first transmission member and is disposed on the other of the gas sensor assembly and the membrane assembly to drive it to move.

In some embodiments, the driving member is a motor, the first transmission member is a screw rod, the second transmission member is a screw nut, and the screw rod and the screw nut are in threaded fit with each other.

In some embodiments, the self-calibrating apparatus for the sensor further includes a manual adjustment assembly disposed on the gas sensor assembly or the membrane assembly, and the manual adjustment assembly is in transmission fit with the first transmission member.

In some embodiments, the manual adjustment assembly includes a mounting base and a manual adjustment member. The mounting base is mounted on the gas sensor assembly or the membrane assembly. The manual adjustment member is mounted on the mounting base, and the manual adjustment member is in transmission fit with the first transmission member and is arranged along the axial direction of the second transmission member.

In some embodiments, the self-calibrating apparatus for the sensor further includes a first travel distance monitor disposed on one of the gas sensor assembly and the membrane assembly. The first travel distance monitor is electrically connected to the driving assembly. When the gas sensor assembly comes into gas-tight contact with the membrane assembly, the other of the gas sensor assembly and the membrane assembly triggers the first travel distance monitor and the first travel distance monitor sends a first in-position signal to the driving assembly to stop it from driving the relative motions between the gas sensor assembly and the membrane assembly.

In some embodiments, the self-calibrating apparatus for the sensor further includes a second travel distance monitor disposed on the other of the gas sensor assembly and the membrane assembly. The second travel distance monitor is electrically connected to the driving assembly. When the gas sensor assembly and the membrane assembly are separated from each other by a predetermined gap distance (usually around one to three centimeters where it is neither too small such that gas cannot efficiently diffuse through, nor too large that it takes unnecessarily long before the gap distance is reached), the other of the gas sensor assembly and the membrane assembly triggers the second travel distance monitor and the second travel distance monitor sends a second in-position signal to the driving assembly to stop it from driving the relative motions between the gas sensor assembly and the membrane assembly.

In some embodiments, the gas sensor assembly includes a mounting plate, one or more electrochemical sensors, a connecting member and a pressing plate. The one or more electrochemical sensors are disposed on the mounting plate. The mounting plate is disposed opposite to the membrane assembly. The connecting member penetrates through the membrane assembly, is connected to the mounting plate at one end thereof, and is connected to the pressing plate at the other end thereof. The first travel distance monitor is disposed on the mounting plate, and the second travel distance monitor is disposed on the membrane assembly and faces the pressing plate.

In some embodiments, the first travel distance monitor and the second travel distance monitor both include a monitoring switch and an elastic touch control member that is disposed on the monitoring switch. The elastic touch control member of the first travel distance monitor protrudes towards the membrane assembly, and the elastic touch control member of the second travel distance monitor protrudes towards the pressing plate.

In some embodiments, the number of the driving assembly is at least two, and the at least two driving assemblies are disposed at both ends of the gas sensor assembly along a long side of the gas sensor assembly.

Additional aspects and advantages of the present disclosure are given partially in the description below, and partially will become apparent from the description below or are learned from practice of the present disclosure.

BRIEF DESCRIPTION OF DRAWINGS

The above and/or additional aspects and advantages of the present disclosure will become apparent and readily appreciated from the description of embodiments in conjunction with the accompanying drawings, in which.

REFERENCE NUMERALS

Figure 1:
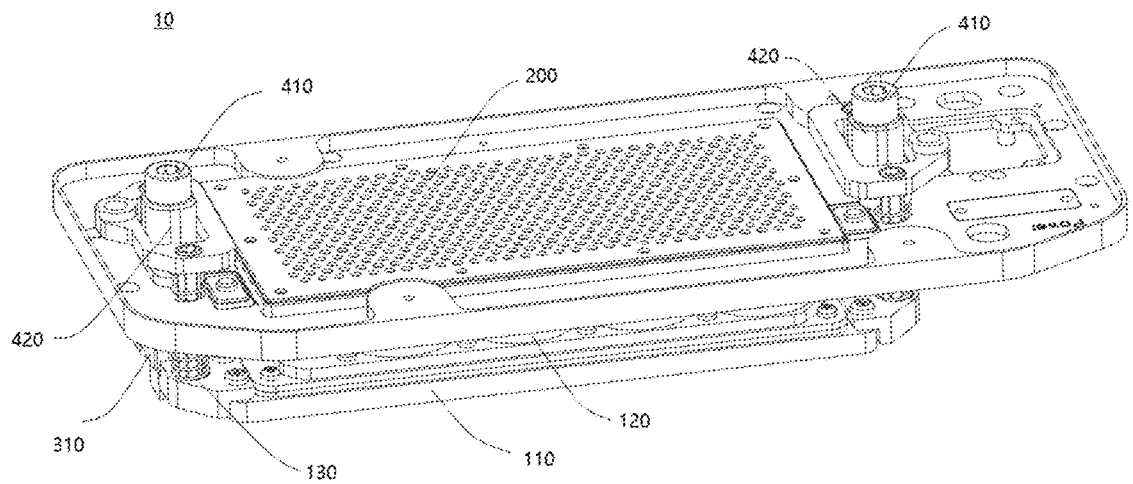
FIG. 1 is a schematic diagram showing a structure of a self-calibrating apparatus for a sensor according to an embodiment of the present disclosure.

Self-calibrating apparatus for a sensor 10, Gas sensor assembly 100, Mounting plate 110, Electrochemical sensor 120, Connecting member 130, Pressing plate 140, Membrane module 200, Driving assembly 300, Driving member 310, First transmission member 320, Second transmission member 330, Manual adjustment assembly 400, Mounting base 410, Manual adjustment member 420, First travel distance monitor 500, Second travel distance monitor 600, Monitoring switch 700, Elastic touch control member 800.

DETAILED DESCRIPTION OF THE DRAWINGS

Hereinafter, embodiments of the present disclosure will be described in detail. The embodiments described below with reference to the accompanying drawings are exemplary. Embodiments of the present disclosure will be described in detail below.

A self-calibrating apparatus 10 for a sensor according to an embodiment of the present disclosure will be described below with reference to FIGS. 1 to 5. For example, the self-calibrating apparatus 10 disclosed in the present application can be applied to one or more electrochemical gas sensors, etc. The self-calibrating apparatus 10 includes a gas sensor assembly 100, a membrane assembly 200 and a driving assembly 300.

Specifically, the membrane assembly 200 is disposed opposite to the gas sensor assembly 100. The driving assembly 300 is disposed between the gas sensor assembly 100 and the membrane assembly 200, and is configured to selectively connect the membrane assembly 200 with the gas sensor assembly 100 or separate the membrane assembly 200 from the gas sensor assembly 100.

It can be understood that when the self-calibrating apparatus 10 of the sensor operates, the gas sensor assembly 100 can sense and analyze specific target gases in the ambient air. In addition, the membrane assembly 200 can move relative to the gas sensor assembly 100 under the control of the driving assembly 300, so that a membrane made of a special material which is attached on the membrane assembly can selectively cover or expose an air permeable surface of the sensor and therefore can selectively filter gases entering the gas sensor assembly 100. In this way, the gas sensor assembly 100 can sense the influence of different gas components in the ambient air under the control of a user or computer routine.

The operation process of the self-calibrating apparatus 10 for the sensor involves at least two detection modes, i.e., a detection mode when the membrane assembly 200 is in "gas-tight" contact with the gas sensor assembly 100 and another mode when the membrane assembly 200 is separated from the gas sensor assembly 100. By "gas-tight", we mean that ambient gas components come into contact with the sensor if and only if they can successfully permeate through the membrane; anything that cannot manage that will not get into the gas sensors through e.g. the peripheral. When the membrane assembly 200 is in gas-tight contact with the gas sensor assembly 100, the membrane assembly 200 filters certain gas components in ambient air so as to only allow gas components that can permeate through the membrane assembly to come into contact with the gas sensor. In this way, the gas sensor can be responsive to the influence of these gas components on the sensor output signal. When the membrane assembly 200 is however separated from the gas sensor assembly 100, the membrane assembly 200 cannot perform the filtration as described above, and the gas sensor therefore can detect/be responsive to all the gas components in the ambient air. By combining these two detection results and using appropriate calculation formulas, the influences of some interference gases in the air can be eliminated, so as to obtain more accurate results for the concentration of the target gas.

In some specific embodiments, the membrane assembly 200 is provided with a proton exchange membrane. The proton exchange membrane can allow water molecules in the ambient air to efficiently permeate through but can prevent most trace gas molecules, especially the hydrophobic ones, from permeating through. That is to say, when the membrane assembly 200 comes into gas-tight contact with the gas sensor assembly 100, water molecules in the ambient air can still enter the gas sensor assembly 100 and affect the output signal of the sensor. This way, the impact by the change of ambient relative humidity on the sensor signal can be captured and later corrected for by proper algorithms. When the membrane assembly 200 is separated from the gas sensor assembly 100, not only the water molecules but also the other trace gas molecules in the ambient air can enter the sensor and be sensed. By combining these two detection results and using appropriate calculation formulas, sensor signal caused by the change in relative humidity can be eliminated, and a signal representing the target trace gas can be obtained, improving the accuracy of the measurement of the concentrations of the target gases.

In other specific embodiments, the membrane assembly 200 is provided with a PET (polyester, such as polyethylene terephthalate) membrane. This type of polyester membrane can prohibit all gas components in the air, including water molecules as mentioned above, from permeating through and therefore can prevent all such molecules from affecting the output signal of the sensor. At this point, the sensor response signal is determined by a sensor baseline as well as ambient temperature, and can be used to design algorithms for corrections of both in later measurements.

It can be understood that the membrane assembly 200 used in the present disclosure can alternatively be composed of other membrane materials, so long as it can help achieve separation of the various gaseous components coexisting in the ambient air. Any such membrane with the above-mentioned properties should fall within the protection scope of the present disclosure and details thereof are omitted here.

With the self-calibrating apparatus 10 for the sensor according to the embodiments of the present disclosure, the driving assembly 300 can move the membrane assembly 200 to cause it to come into gas-tight contact with or be separated from the gas sensor assembly 100, thus the membrane assembly 200 can selectively filter the air components that enter the gas sensor assembly 100, and the gas sensor assembly 100 can obtain different detection results based on different air components that enter and be detected by it. In this way, these detection results probing the effects of the different gas components on sensor output signal can be combined and finally utilized to allow for the accurate calibration of the response of the gas sensor assembly 100 to the constantly changing ambient temperature and relative humidity and zero-line position and so on, reducing the error level and improving the gas detection accuracy by the gas sensor assembly 100.

Figure 4:
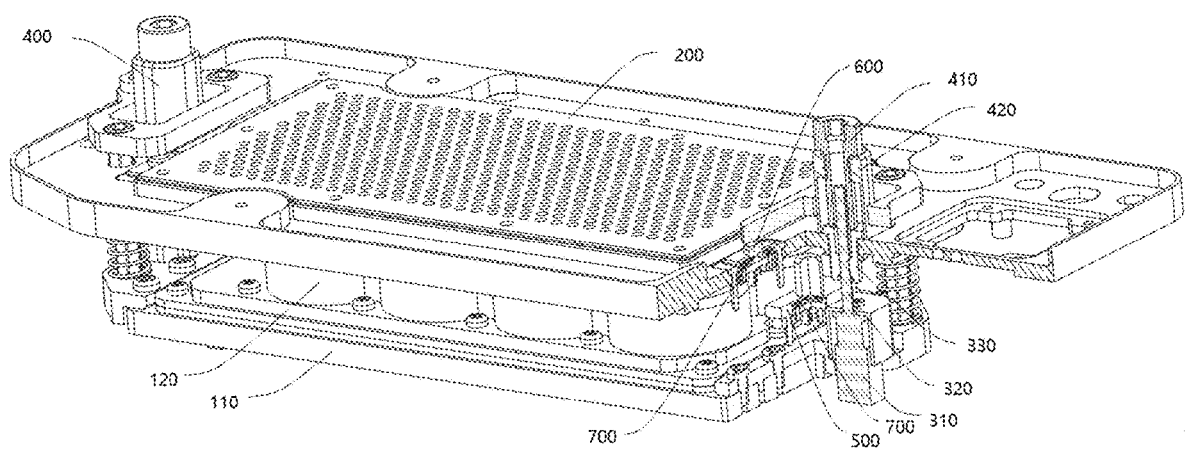
FIG. 4 is a schematic cross-sectional view showing a structure of a self-calibrating apparatus for a sensor according to an embodiment of the present disclosure.
Figure 5:
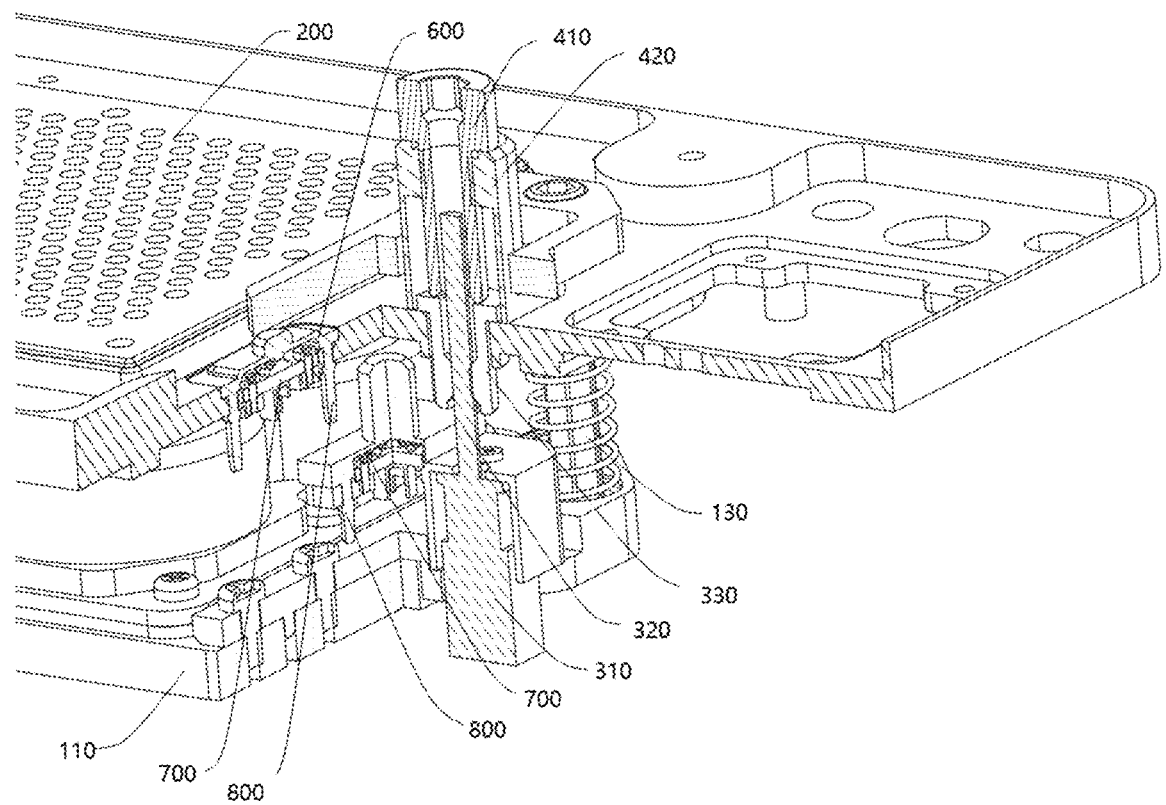
FIG. 5 is a schematic enlarged cross-sectional view showing a structure of a self-calibrating apparatus for a sensor according to an embodiment of the present disclosure.

In some embodiments, as shown in FIGS. 4 and 5, the driving assembly 300 includes a driving member 310, a first transmission member 320 and a second transmission member 330. The driving member 310 is disposed on one of the gas sensor assembly 100 and the membrane assembly 200. The first transmission member 320 is disposed on the driving member 310. The second transmission member 330 is in transmission fit with the first transmission member 320. The second transmission member 330 is disposed on the other of the gas sensor assembly 100 and the membrane assembly 200 to drive the other of the gas sensor assembly 100 and the membrane assembly 200 to move.

It can be appreciated that the driving member 310 provides a driving force to drive the membrane assembly 200 to be in gas-tight contact with or separated from the gas sensor assembly 100. The driving force is transmitted to the second transmission member 330 through the first transmission member 320 to drive the gas sensor assembly 100 and the membrane assembly 200 to move relative to each other, so as to enable the membrane assembly 200 and the gas sensor assembly 100 to be in gas-tight contact with or separated from each other under the control of a user or computer routine. In this way, the membrane assembly 200 can filter gases entering the gas sensor assembly 100 to allow for the isolation of their individual effects on the gas sensors as well as determination of gas sensor baselines.

In some specific embodiments, the driving member 310 is a motor, the first transmission member 320 is a screw rod, the second transmission member 330 is a screw nut, and the screw rod and the screw nut are in threaded fit with each other. That is, the transmission between the first transmission member 320 and the second transmission member 330 is in a lead-screw transmission mode, which can conveniently induce the relative movement between the membrane assembly 200 and the gas sensor assembly 100, and can reliably achieve the gas-tight contact between the membrane assembly 200 and the gas sensor assembly 100 or the separation of the two. In this way, more accurate detection of the target gases by the gas sensor assembly 100 can be achieved (in conjunction with proper processing of the calibration stage data and algorithm design).

Figure 2:
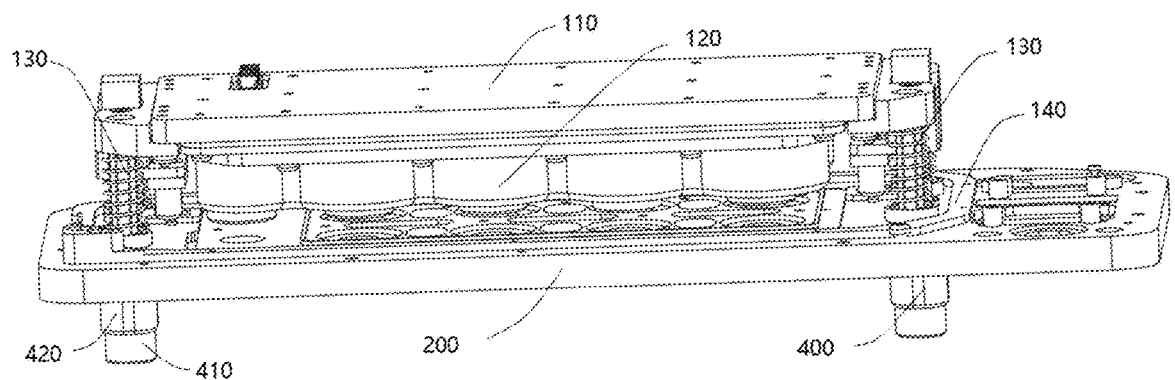
FIG. 2 is a schematic diagram showing a structure of a self-calibrating apparatus for a sensor according to an embodiment of the present disclosure.
Figure 3:
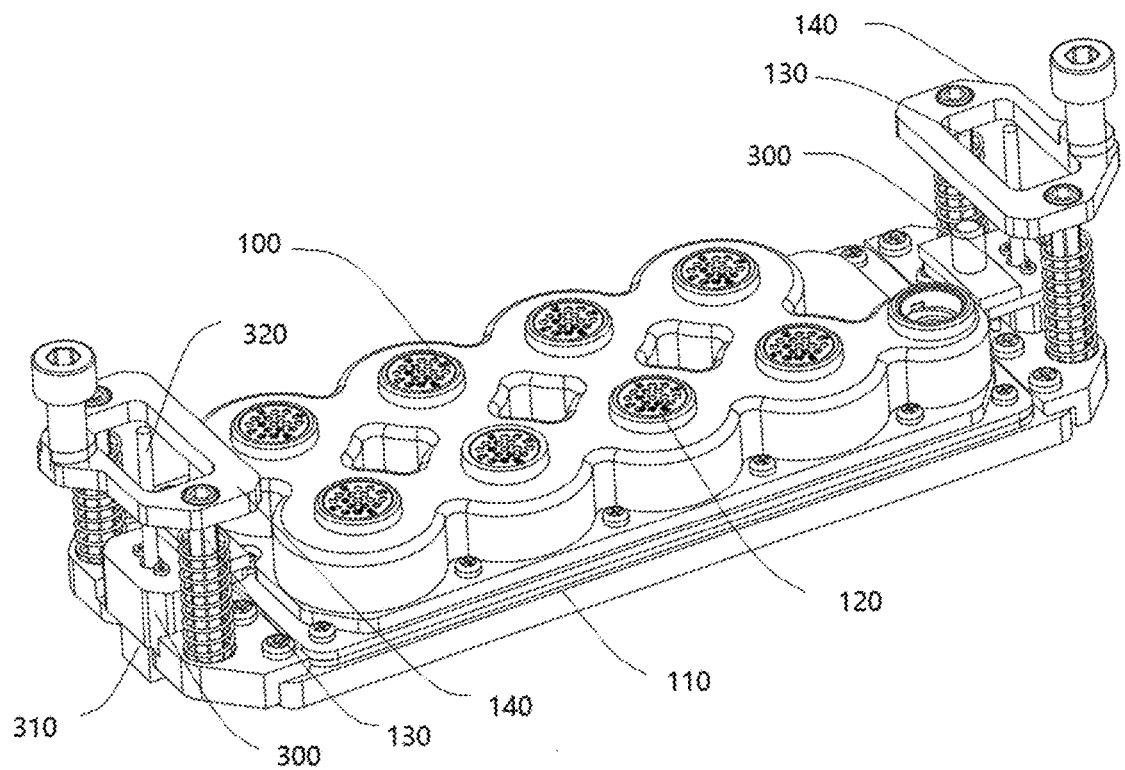
FIG. 3 is a schematic diagram showing a portion of a structure of a self-calibrating apparatus for a sensor according to an embodiment of the present disclosure.

In some embodiments, as shown in FIGS. 1, 2 and 3, the self-calibrating apparatus for the sensor further includes a manual adjustment assembly 400 disposed on the gas sensor assembly 100 or the membrane assembly 200. The manual adjustment assembly 400 is in transmission fit with the first transmission member 320. By providing the manual adjustment component 400 on the self-calibrating apparatus 10 for the sensor, when the electric driving assembly 300 ceases to function properly due to e.g. electrical or mechanical failures, the user or computer routine can use the manual adjustment assembly 400 to drive the first transmission assembly 320 and thereafter the membrane assembly 200 to move, thereby achieving gas-tight contact of the membrane assembly 200 and the gas sensor assembly 100 or the separation of the two via manual turning. In summary, this enables the self-calibrating apparatus 10 for the sensor to be adjusted by manually adjusting the manual adjustment assembly 400, so that the self-calibrating apparatus 10 for the sensor can continue working when the driving assembly 300 fails, thereby improving the robustness of the self-calibrating apparatus 10 for the sensor.

In some embodiments, as shown in FIGS. 1, 2 and 3, the manual adjustment assembly 400 includes a mounting base 410 and a manual adjustment member 420. The mounting base 410 is mounted on the gas sensor assembly 100 or the membrane assembly 200, the manual adjustment member 420 is mounted on the mounting base 410, and the manual adjustment member 420 is in transmission fit with the first transmission member 320 and is arranged along an axial direction of the second transmission member 330. It can be understood that the mounting base 410 provides the mounting point for the manual adjustment member 420, facilitating the assembly of the manual adjustment member 420. At the same time, due to the axial arrangement of the manual adjustment member 420 and the second transmission member 330, when the manual adjustment member 420 works together with the first transmission member 320, the rotation of the manual adjustment member 420 can be transferred to the second transmission member 330 through the first transmission member 320, thereby achieving the manual driving of the second transmission member 330 which ultimately drives the membrane component 200 to move, thus improving the applicability of the self-calibrating apparatus 10 for the sensor.

In some embodiments, as shown in FIGS. 4 and 5, the self-calibrating apparatus 10 for the sensor further includes a first travel distance monitor 500 disposed on one of the gas sensor assembly 100 and the membrane assembly 200. The first travel distance monitor 500 is electrically connected to the driving assembly 300. When the gas sensor assembly 100 comes into gas-tight contact with the membrane assembly 200, the other of the gas sensor assembly 100 and the membrane assembly 200 triggers the first travel distance monitor 500, prompting it to send a first in-position signal to the driving assembly 300 which instructs this assembly to stop outputting driving force, thereby avoiding any motor overheating and/or unnecessary mechanical strain. In this way, the lifespan and reliability of the self-calibrating apparatus 10 for the sensor can be increased.

In some embodiments, as shown in FIGS. 4 and 5, the self-calibrating apparatus 10 for the sensor further includes a second travel distance monitor 600 disposed on the other of the gas sensor assembly 100 and the membrane assembly 200. The second travel distance monitor 600 is also electrically connected to the driving assembly 300. When the gas sensor assembly 100 and the membrane assembly 200 are separated from each other by a predetermined gap distance, the other of the gas sensor assembly 100 and the membrane assembly 200 triggers the second travel distance monitor 600, prompting it to send a second in-position signal to the driving assembly 300 which asks this assembly to stop outputting driving force. This, as described above, avoids motor overheating and unnecessary mechanical strain and again improves the lifespan and reliability of the self-calibrating apparatus 10.

In some embodiments, as shown in FIGS. 1, 2 and 3, the gas sensor assembly 100 includes a mounting plate 110, one or more electrochemical sensors 120, a connecting member 130 and a pressing plate 140. The one or more electrochemical sensors 120 are disposed on the mounting plate 110, and the mounting plate 110 is disposed opposite to the membrane assembly 200. The connecting member 130 penetrates through the membrane assembly 200, connected to the mounting plate 110 at one end thereof and to the pressing plate 140 at the other end thereof. The first travel distance monitor 500 is disposed on the mounting plate 110, and the second travel distance monitor 600 is disposed on the membrane assembly 200 and faces the pressing plate 140. In this way, the mounting plate 110 acts as the base for the mounting of the assembly of the one or more electrochemical sensors 120. The connecting member 130 is made of rods of equal lengths that connect the mounting plate 110 with the pressing plate 140, so this length effectively determines the gap distance between the two. Springs can be sleeved outside the connecting rods to make the entire axial movement more steady.

In some embodiments, as shown in FIGS. 4 and 5, the first travel distance monitor 500 and the second travel distance monitor 600 both include a monitoring switch 700 and an elastic touch control member 800 that is disposed on the monitoring switch. The elastic touch control member 800 of the first travel distance monitor 500 protrudes towards the membrane assembly 200, and the elastic touch control member 800 of the second travel distance monitor 600 protrudes towards the pressing plate 140. The monitoring switch 700 is turned on when the elastic touch control member 800 abuts against it, and a trigger signal can then be produced and sent to the driving assembly 300. This design of the first travel distance monitor 500 and the second travel distance monitor 600 is simple, and the first travel distance monitor 500 and the second travel distance monitor 600 can achieve an effective in-position indication function.

In some specific embodiments, the number of the driving assembly 300 is at least two, and the at least two driving assemblies 300 are disposed at both ends of the gas sensor assembly 100 along its long side. In this way, the driving assembly 300 can drive the membrane assembly 200 to move steadily.

Other configurations and operations of the self-calibrating apparatus 10 for the sensor according to embodiments of the present disclosure are known to the person of ordinary skills in the field, and details thereof are omitted here.

In the illustration of this description, an illustration with reference to the terms "one embodiment", "some embodiments", "illustrative embodiments", "an example", "a particular example" or "some examples" and so on mean that a particular feature, structure, material, or characteristic described in connection with the embodiment(s) or example(s) is included in at least one embodiment or example of the present disclosure. In this description, the exemplary expressions of the above terms do not necessarily specify the same embodiments or examples.

Although embodiments of the present disclosure have been shown and described, it will be understood by those skilled in the art that various changes, modifications, alternations and variations may be made to these embodiments without departing from the principles and spirit of the present disclosure, the scope of which is defined by the claims and their equivalents.

What is claimed is:

1. An apparatus for a sensor for self calibration, comprising:
   a gas sensor assembly, comprising a plurality of gas sensors arranged in a two-dimensional array;
   a membrane assembly disposed opposite to the gas sensor assembly; and
   a driving assembly disposed between the gas sensor assembly and the membrane assembly and configured to selectively connect the membrane assembly with the gas sensor assembly or to separate the membrane assembly from the gas sensor assembly; wherein the membrane assembly is plate-shaped and adapted to selectively cover the plurality of gas sensors.

2. The apparatus according to claim 1, wherein the driving assembly comprises:
   a driving member;
   a first transmission member; and
   a second transmission member, wherein the driving member is disposed on one of the gas sensor assembly and the membrane assembly, the first transmission member is disposed on the driving member, and the second transmission member is in transmission fit with the first transmission member and is disposed on the other of the gas sensor assembly and the membrane assembly to drive the other of the gas sensor assembly and the membrane assembly to move.

3. The apparatus according to claim 2, wherein the driving member is a motor, the first transmission member is a screw rod, the second transmission member is a screw nut, and the screw rod and the screw nut are in threaded fit with each other.

4. The apparatus according to claim 2, further comprising:
   a manual adjustment assembly disposed on the gas sensor assembly or the membrane assembly, and the manual adjustment assembly is in transmission fit with the first transmission member.

5. The apparatus according to claim 4, wherein the manual adjustment assembly comprises a mounting base and a manual adjustment member, the mounting base is mounted on the gas sensor assembly or the membrane assembly, the manual adjustment member is mounted on the mounting base, and the manual adjustment member is in transmission fit with the first transmission member and is arranged along an axial direction of the second transmission member.

6. The apparatus according to claim 1, further comprising a first travel distance monitor disposed on one of the gas sensor assembly and the membrane assembly, the first travel distance monitor is electrically connected to the driving assembly, and when the gas sensor assembly comes into gas-tight contact with the membrane assembly, the other of the gas sensor assembly and the membrane assembly triggers the first travel distance monitor and the first travel distance monitor sends a first in-position signal to the driving assembly to stop it from driving the relative motions between the gas sensor assembly and the membrane assembly.

7. The apparatus according to claim 6, further comprising a second travel distance monitor disposed on the other of the gas sensor assembly and the membrane assembly, the second travel distance monitor is electrically connected to the driving assembly, and when the gas sensor assembly and the membrane assembly are separated from each other by a predetermined gap distance, the other of the gas sensor assembly and the membrane assembly triggers the second travel distance monitor and the second travel distance monitor sends a second in-position signal to the driving assembly to stop it from driving the relative motions between the gas sensor assembly and the membrane assembly.

8. The apparatus according to claim 7, wherein the gas sensor assembly comprises a mounting plate, a plurality of electrochemical sensors, a connecting member and a pressing plate, the plurality of electrochemical sensors are disposed on the mounting plate, the mounting plate is disposed opposite to the membrane assembly, the connecting member penetrates through the membrane assembly and is connected to the mounting plate at one end thereof and to the pressing plate at the other end thereof, the first travel distance monitor is disposed on the mounting plate, and the second travel distance monitor is disposed on the membrane assembly and faces the pressing plate.

9. The apparatus according to claim 8, wherein the first travel distance monitor and the second travel distance monitor both comprise a monitoring switch and an elastic touch control member that is disposed on the monitoring switch, and the elastic touch control member of the first travel distance monitor protrudes towards the membrane assembly, while the elastic touch control member of the second travel distance monitor protrudes towards the pressing plate.

10. The apparatus according to claim 1, wherein the number of the driving assembly is at least two, and the at least two driving assemblies are disposed at both ends of the gas sensor assembly along a long side of the gas sensor assembly.

* * * * *